United States Patent
Hübschen et al.

(10) Patent No.: US 7,434,467 B2
(45) Date of Patent: Oct. 14, 2008

(54) ELECTROMAGNETIC ULTRASOUND CONVERTER

(75) Inventors: Gerhard Hübschen, Saarlouis (DE); Frank Niese, Saarbrucken (DE); Alexander Viskov, Saarbrucken (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 249 days.

(21) Appl. No.: 10/539,818

(22) PCT Filed: Dec. 6, 2003

(86) PCT No.: PCT/EP03/13857

§ 371 (c)(1), (2), (4) Date: Feb. 28, 2006

(87) PCT Pub. No.: WO2004/058420

PCT Pub. Date: Jul. 15, 2004

(65) Prior Publication Data

US 2006/0173341 A1 Aug. 3, 2006

(30) Foreign Application Priority Data

Dec. 20, 2002 (DE) .............................. 102 59 891

(51) Int. Cl.
*G01N 29/24* (2006.01)

(52) U.S. Cl. .................................................. 73/643

(58) Field of Classification Search .................... 73/643
See application file for complete search history.

(56) References Cited

U.S. PATENT DOCUMENTS 6,009,756 A * 1/2000 Willems et al. ............... 73/643

FOREIGN PATENT DOCUMENTS

| DE | 41 30 935 A1 | 3/1993 |
|----|---|---|
| DE | 42 28 426 C1 | 3/1994 |
| DE | 195 43 481 A1 | 5/1997 |
| EP | 0 440 317 A1 | 8/1991 |
| EP | 0 579 255 B1 | 1/1994 |

* cited by examiner

*Primary Examiner*—John E Chapman
(74) *Attorney, Agent, or Firm*—Antonelli, Terry, Stout & Kraus, LLP.

(57) ABSTRACT

An electromagnetic ultrasonic transducer for coupling-media-free generation and/or reception of ultrasonic waves in the form of linearly polarized transverse waves in and from a workpiece is disclosed, having at least one unit which converts the ultrasonic waves inside the workpiece and which is provided with a coil for generating, and/or detecting a high-frequency magnetic field and premagnetizing unit for generating a quasi-static magnetic field which superimposes the high-frequency magnetic field in the workpiece The coil is disposed in a torus-shape on at least one partially toroidal or U-shaped magnetic core, having two front ends which can be turned to face the workpiece. The front ends of the magnetic core, which can be turned to face the workpiece, are connected directly or indirectly to a magnetic flux piece which has a surface facing the workpiece and connecting the front ends with each other.

30 Claims, 7 Drawing Sheets

ELECTROMAGNETIC ULTRASOUND CONVERTER

BACKGROUND OF THE INVENTION

1. Field of the Invention

The present invention relates to an electromagnetic ultrasonic transducer for coupling media free generation and/or reception of ultrasonic waves in the form of linearly polarized transverse waves into, and from, a workpiece having at least one unit that converts the ultrasonic waves inside the workpiece. The unit has a coil arrangement for generating, and/or detecting, a high-frequency (HF) magnetic field and a premagnetizing unit for generating a quasi-static magnetic field which superimposes the HF magnetic field in the work piece, with the coil arrangement being torus shaped on at least one partially toroidal or U-shaped magnetic core which has two front ends which can each be turned to face the workpiece.

These ultrasonic probes permit generating and receiving linearly polarized transverse waves, which preferably are irradiated under the probe perpendicularly into the workpiece, and are received from this direction and oscillate preferably perpendicular to their propagation direction. Technical fields of application of such type ultrasonic probes are, for example, nondestructive examination of electrically conductive workpieces for material flaws, such as for example cracks, in particular crack-like flaws oriented parallel to the polarization direction of the ultrasonic waves and perpendicular to the propagation direction, as well as other processes based on ultrasonic velocity and polarization, such as for example measuring voltage or, in particular, measuring thickness.

2. Description of the Prior Art

The coupling media free electromagnetic probes known in the art convert electromagnetic field energies into elastic energy of an ultrasonic wave and inversely. The conversion mechanism is based on the interaction between the electromagnetic field and an electrically conducting material that also has a static magnetic field or a quasi-static magnetic field applied from the outside which passes through the conducting material. The term "quasi-static" magnetic field comprises, in addition to the actual static magnetic field, which for example can be generated by means of permanent magnets, also low-frequency magnetic fields, whose alternating frequency is much lower than the high frequency with which the coil arrangement is operated to generate high-frequency fields.

In order to excite ultrasonic waves inside an electrically conducting workpiece, at least one part of the high-frequency magnetic field, whose frequency range lies within the ultrasonic frequency range, generated by the high-frequency coil arrangement, is coupled into the workpiece, thus inducing eddy currents at skin depth, which if superimposed on the "quasi-static" magnetic field, generate ultrasonic waves due to the Lorentz forces or magnetostrictions occurring inside the workpiece.

Detection of ultrasonic waves occurring inside the workpiece occurs inversely by detection of the electrical voltage induced inside the coil arrangement resulting from high-frequency fields which for their part are generated by the motions of electric charges, due to the ultrasonic waves, in the workpiece inside the "quasi-static" magnetic field.

All prior art electromagnetic ultrasonic transducers are based on optimizing measuring sensitivity and, related thereto, the signal amplitudes of both the transmission signal and in the reception signal that can be generated with the coil arrangements. The goal, on the one hand, is to design the coupling mechanism with which the generated and to-be-detected high-frequency fields are coupled into and out of the ultrasonic transducer and the workpiece as loss-free as possible and, on the other hand, to select the field strength of the quasi-static magnetic field as large as possible, which is decisive for generating and detecting ultrasonic waves.

German Patent DE 42 23 470 C2 describes a generic electromagnetic probe for vertical acoustic irradiation of linearly polarized transverse waves, in which the high-frequency magnetic fields are coupled into and out of in a most efficient manner between the probe and the workpiece without, as is the case with many other probes, placing the transmission and reception coils (usually designed as high-frequency air coils) directly on the surface of the workpiece. But rather the electromagnetic probe of FIG. 2 described in this printed publication is provided with a half-open toroidal tape core 1, made commercially of amorphous tape material, around which a transmission coil 41 and a reception coil 42, respectively, are wound. The front ends 2 of the half-open toroidal core 1 act as coupling areas for the high-frequency magnetic fields and can be placed on the surface of the workpiece 7. The high-frequency magnetic fields generated by the high-frequency transmission coil arrangement 41 reach, via the front ends 2 of the toroidal core 1, into the workpiece 7 and are able to induce the surface eddy currents 8 at skin depth inside the workpiece 7.

The quasi-static magnetic field oriented perpendicular to the surface of the workpiece 7 required for sound conversion is generated by means of two permanent magnets 6 of the same name and conveyed to the material surface of the workpiece 7. The premagnetizing unit required for producing the "quasi-static" magnetic field that is oriented perpendicular to the surface of the workpiece is located inside the open part of the toroidal core 1. With this arrangement, ultrasonic waves with a propagation direction A perpendicular to the surface of the workpiece and an oscillation plane S perpendicular thereto develop inside the workpiece.

German Patent DE 41 30 935 A1 describes a probe device comparable to this arrangement. However, in this probe device the transmission and reception coil arrangement lies directly on the surface of the workpiece to-be-examined, which has the danger of coil wear.

German Patent DE 195 43 482 A1 describes a device for testing ferromagnetic materials, preferably in the form of pipe lines. However, this device has a component setup that differs from the state of the art described in detail in the preceding and on which the following is based.

SUMMARY OF THE INVENTION

Based on the aforementioned state of the art, the present invention is an electromagnetic ultrasonic transducer which efficiently generates ultrasonic waves with an improved detection sensitivity compared to the prior art ultrasonic transducers. In particular, the coil arrangement is disposed at a distance from the surface of the workpiece in order to be able to prevent mechanical impairment of the coil arrangement. Moreover, the ultrasonic transducer permits generating horizontally polarized ultrasonic waves.

A key element of the present invention is further an electromagnetic ultrasonic transducer for coupling media free generation and/or reception of ultrasonic waves in the form of linearly polarized transverse waves into, and from, a workpiece, having at least one unit which converts the ultrasonic waves inside the workpiece and which is provided with a coil arrangement for generating, and/or detecting, a high-frequency magnetic field as well as a premagnetizing unit for generating a quasi-static magnetic field which is superimposed upon the high-frequency magnetic field in the workpiece, with the coil arrangement being torus-shaped on at least one partially toroidal or U-shaped magnetic core, which has two front ends that can be turned to face the workpiece, so that the front ends of the magnetic core, that can be turned to face the workpiece, are connected directly or indirectly to a magnetic flux guide piece which has a surface facing the workpiece and which connects the front ends with one another.

Providing a flux guide piece connecting the front ends of a magnet core, preferably as a toroidal tape core, with each other, permits, in particular, coupling in the high-frequency magnetic fields generated by the coil arrangement most efficiently into the workpiece in order to be able, in this manner, to generate very distinctive eddy currents at skin depth. For this purpose, the flux guide piece has a surface which preferably conforms with the surface of the workpiece thereby permitting, preferably contour-matching, contacting of the flux guide piece and the workpiece. In a preferred embodiment, the flux guide piece is formed as a rectangular rod with a plane surface facing the workpiece. The plane surface can be placed flush on an equally plane formed workpiece surface without any coupling media. The surface of the flux guide piece facing the workpiece can, of course, be produced, depending on the curvature of the to-be-examined workpieces, in a surface mold matching the contour of the workpiece. If the electromagnetic ultrasonic transducer is to be, for example, utilized preferably for examining cylindrical workpiece surfaces, the flux guide piece connecting the front ends of the toroidal cores is formed corresponding to the contour.

In addition to optimize coupling of the high frequency magnetic field into the workpiece surface by means of the flux guide piece, the flux guide piece is also able to couple the quasi-static magnetic field almost without losses into the workpiece. For this purpose, in a typical preferred embodiment, the premagnetizing unit for generating the quasi-static magnetic field is a permanent magnet, which is disposed directly on the flux guide piece between the front ends of the toroidal core, which projects beyond the permanent magnet. In this case, the flux guide piece acts as a concentrator for the quasi-static, and permanent magnetic field.

In order to prevent eddy currents from developing inside the flux guide piece, it is advantageous to make the flux guide piece out of an electrically nonconductive carrier material into which a matrix of soft magnetic particles are introduced. Alternatively, a stack-shaped arrangement of soft magnetic transformer metal sheets can also effectively prevent eddy currents from developing inside the flux guide piece.

In addition to the electromagnetic ultrasonic transducer whose partially toroidal or U-shaped magnetic core projects beyond a single magnetic flux guide piece, with the front ends of the magnetic core being closely connected to the single flux guide piece, a second, alternative preferred embodiment of an electromagnetic transducer is provided with at least two flux guide pieces disposed side by side in parallel which are connected to each other in a bridge-like manner by at least two partially toroidal or U-shaped magnetic cores via their respective front ends. The magnetic cores are disposed at a distance from each other at the opposite end regions of the rod-shaped flux guide pieces. This manner of construction permits placing the premagnetizing unit, preferably in the form of a permanent magnet arrangement, between the two magnetic cores in a longitudinal direction of the two flux guide pieces without the magnetic cores, preferably as toroidal cores, spanning them as with the previously described preferred embodiment. As a result, the possibilities of scaling the dimensions of the permanent magnet arrangement are practically unlimited, permitting enlarging the magnetic field strength accordingly.

In addition to the simplest preferred embodiment of the magnetic core in the form of a toroidal core wound with at least one coil arrangement, also feasible are magnetic cores with an M-shaped magnetic cross section each having three free-ending front ends. Compared to the preceding electromagnetic ultrasonic transducer arrangement, with such type magnetic cores, three parallel adjacent magnetic flux guide pieces can be connected in a bridge-like manner.

As described in detail further on herein with reference to the following preferred embodiments, linearly polarized transverse waves can be generated inside the workpiece by a multiplicity of the aforedescribed ultrasonic transducers and triggering of the coil arrangements placed on the magnetic cores in a toroidal manner. In particle, corresponding multiple arrangements permit generating vertically or horizontally linearly polarized transverse waves.

For this purpose the electromagnetic ultrasonic transducers according to the present invention as previously described, can be placed side by side in a multiple arrangement in order to obtain, on the one hand, a large as possible a transmitting and receiving aperture and, on the other hand, to obtain, by means of phase-controlled high-frequency excitation of the individual coil arrangements, a selectively settable irradiation characteristic for the ultrasonic waves that can be coupled into the workpiece. As will be described further on herein, such type arrangements are suited for a phased array arrangement for generating horizontally polarized transverse waves (shear horizontal waves) whose propagation direction can be selectively set, which includes with reference to the normal of the workpiece surface a variable angle between 0° and 90°.

BRIEF DESCRIPTION OF THE INVENTION

The present invention is made more apparent in the following with reference to the accompanying drawings by way of example without the intention of limiting the scope or spirit of the invention.

DETAILED DESCRIPTION OF THE INVENTION

Figure 1:
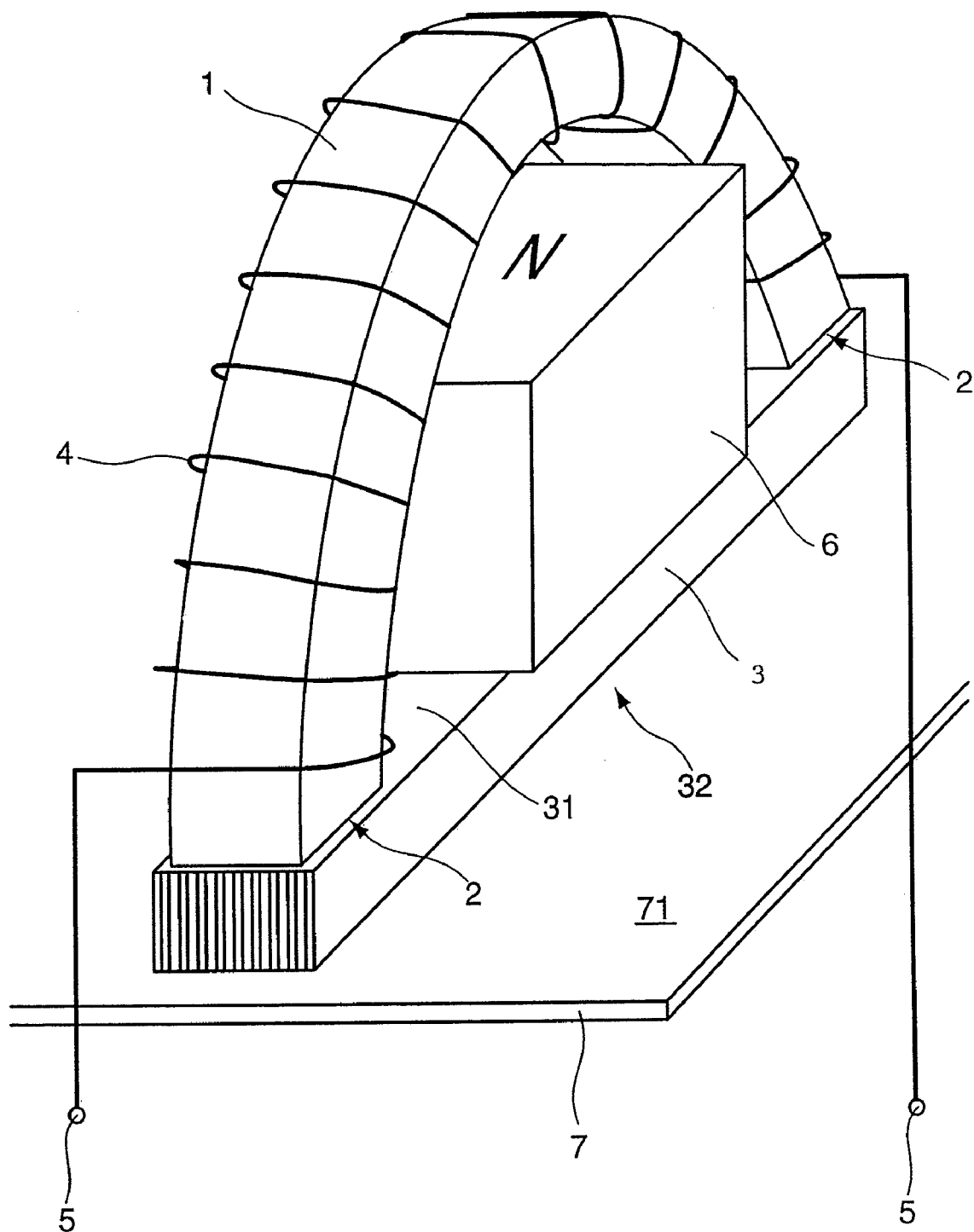
FIG. 1 shows an electromagnetic ultrasonic transducer having a single flux guide piece.

FIG. 1 shows the simplest preferred embodiment of an electromagnetic ultrasonic transducer according to the present invention, in which a partially toroidal magnetic core configured as a half toroidal core 1 with two front ends 2 directly connected to a rod shaped flux guide piece 3 having a rectangular cross section. Wound about the half toroidal core 1 in a torus shape is a coil arrangement 4, which has two connections. Provided directly on the surface 31 of the flux guide piece 3 is a premagnetizing unit 6, which, in the preferred embodiment, is a permanent magnet and has a north pole as indicated. The toroidal core 1 projects completely over the permanent magnet 6. Also only indicated is the workpiece 7 to be examined with the aid of the electromagnetic ultrasonic transducer arrangement and on whose workpiece surface 71, the flux guide piece 3 with its surface 32 facing the workpiece 7 can be placed, preferably with a matching contour. In this manner, the magnetic field generated by means of the permanent magnet 6 enters the workpiece 7 perpendicularly through the flux guide piece 3 via the workpiece surface 71. Alternatively to the embodiment of the premagnetizing unit in the form of a permanent magnet 6, as illustrated in FIG. 1, the premagnetizing unit may be in the form of an electromagnet whose field lines enter the workpiece perpendicular to the workpiece surface in the same manner as in the arrangement depicted in FIG. 1. However, it is also possible to position an electromagnet so that the magnetic field generated by the electromagnet enters the workpiece parallel to the workpiece surface. The effects related to such a magnetic field alignment are described hereinafter.

The electromagnetic ultrasonic transducer shown in FIG. 1 should be viewed as an electromagnetic transducer which can be operated both as an ultrasonic transmitter and an ultrasonic receiver. When transmitting, the connection contacts 5 are connected to a high-frequency generator and when receiving the connection contacts 5 are connected to a corresponding amplifier and a downstream evaluation unit. Of course, two separate coil arrangements, with one acting as a transmission coil and the other acting as a reception coil, can also be provided along a single half toroidal core.

Figure 2:
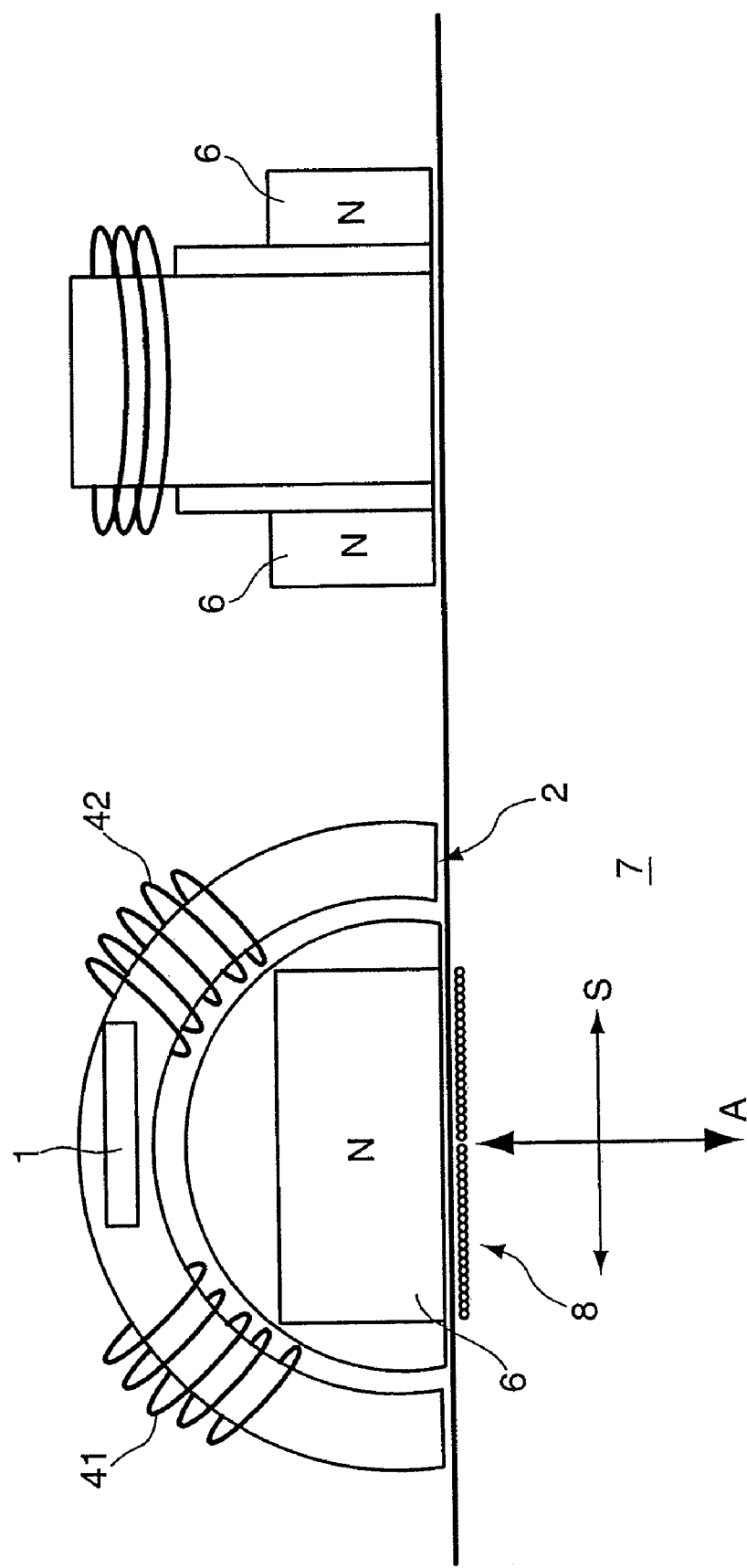
FIG. 2 shows a state-of-the-art electromagnetic ultrasonic transducer.

Due to the large area contact between the lower side 32 of the flux guide piece 3 and the workpiece surface 71 of the workpiece 7, the high-frequency magnetic fields conveyed in the longitudinal direction of the flux guide piece 3 couple into the workpiece 7 along the entire longitudinal extension of the flux guide piece 3 and generate intensive eddy currents at skin depth. These eddy currents, interact with the quasi-static magnetic field passing through the workpiece surface 71 and generate, due to the developing Lorentz forces and magnetostrictions, ultrasonic waves with a frequency corresponding to the alternating frequency of the high-frequency magnetic fields. Due to the close contact between the flux guide piece 3 and the workpiece surface 71, a higher magnetic flux is generated inside the workpiece 7 than is the case with the hitherto known electromagnetic ultrasonic transducers, for example as illustrated in FIG. 2. In this manner, the effectiveness of generation of the ultrasonic waves and the sensitivity of the reception can be increased considerably.

The preferred embodiment of an electromagnetic ultrasonic transducer shown in FIG. 1, in which the quasi-static magnetic field passes perpendicularly through the workpiece surface 71, permits generating linearly polarized transverse waves whose propagation direction is oriented perpendicular to the surface of the workpiece and has an oscillation plane oriented perpendicular to the propagation direction.

Figure 3:
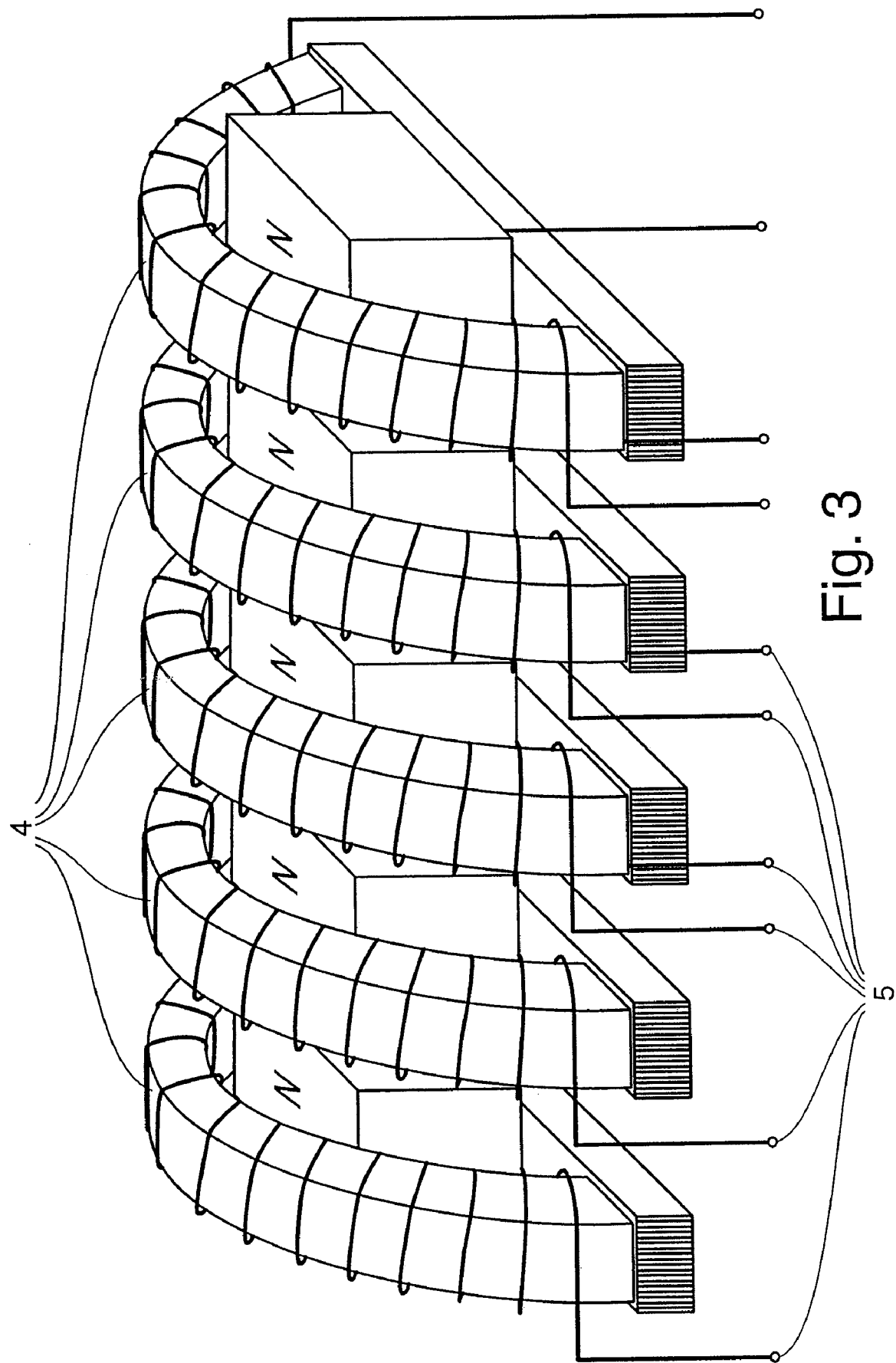
FIG. 3 shows an arrangement of a multiplicity of single electromagnetic ultrasonic transducers according to the embodiment of FIG. 1.

Selective excitation of horizontally polarized transverse waves (shear horizontal waves) requires, in a known manner, a premagnetizing unit, usually in the form of an arrangement of permanent magnets with an alternating polarity whose alternating magnetic fields superimpose a high-frequency magnetic field inside the workpiece. FIG. 3 shows an arrangement designed according to the present invention, for generating horizontally polarized transverse waves, which, in the illustrated preferred embodiment, is provided with five parallel electromagnetic line transducers arranged adjacent to each other according to the example shown in FIG. 1. It is assumed that the coil arrangements 4, as illustrated in FIG. 3, on each of the singly illustrated ultrasonic transducers are designed for generating and for receiving ultrasonic waves. If the electrical connections 5 of the individual coil arrangements 4 for transmitting and receiving are connected to separate electronic channels of a high-frequency generator, and of a corresponding amplifier, and if the individual electronic channels are operated in a time-delayed manner in their triggering phase, a phased array arrangement which is able to generate and detect horizontally polarized transverse waves inside the workpiece—like a group radiator—can be achieved with the arrangement illustrated in FIG. 3. Adjacently disposed ultrasonic transducers operated with a magnetic flux directed in the opposite direction in the flux guide piece, thereby generating alternating eddy current directions under the adjacent flux guide pieces. This causes Lorentz forces directed in opposite directions and the related magnetostriction directions. In this manner shear forces are generated to produce horizontally polarized transverse waves inside the workpiece.

Figure 4:
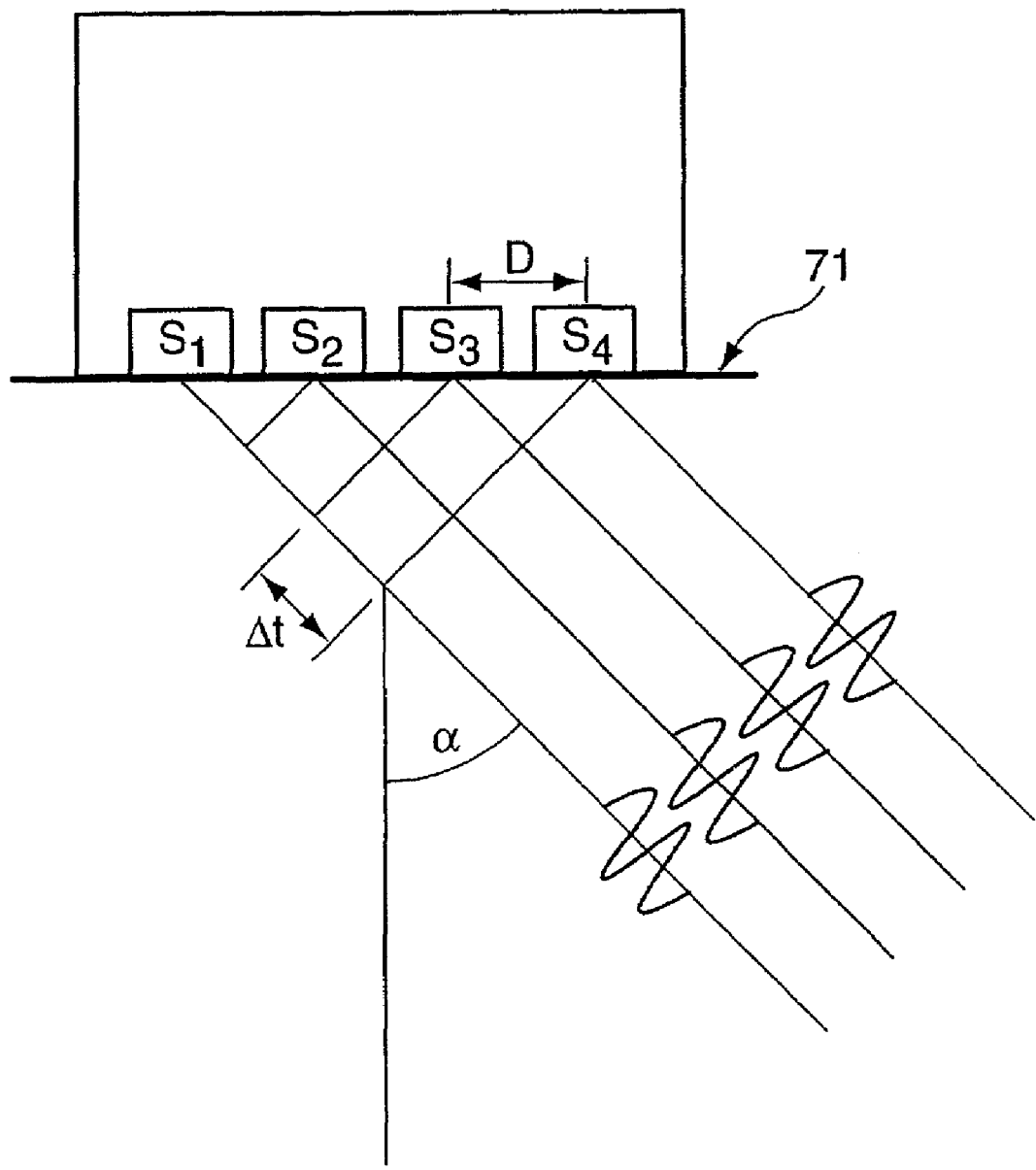
FIG. 4 shows a schematic representation of an ultrasonic wave field generated inside a workpiece by the arrangement according to FIG. 3.

Suitable selection of the phase-dependent triggering of the individual ultrasonic transducers disposed side by side in a row permits selectively setting the direction characteristic of the developing horizontally polarized transverse waves. In this manner the main propagation direction of the main lobe of the horizontally polarized transverse waves form an angle α, selectable from 0° to 90° as desired, with the surface normal of the surface of the workpiece. FIG. 4 shows an illustrative sketch of a system for generating horizontally polarized transverse waves with the aid of the ultrasonic wave arrangement illustrated in FIG. 3. It is assumed that four ultrasonic transducers $S_1$-$S_4$ are disposed side by side at a distance D from each other on the workpiece surface 71. A current pulse is applied to the individual ultrasonic transducers $S_1$-$S_4$ at an interval of Δt in the aforedescribed manner. Due to the phase-delayed application of current to the ultrasonic transducers $S_1$-$S_4$, horizontally polarized transverse waves develop inside the workpiece. These transverse waves have a main propagation direction that forms with the normals of the surface of the workpiece an angle α, for which $$\alpha = \sin(c_t \cdot \Delta t / D)$$

applies.

In the above equation $c_t$ represents for the propagation velocity of the horizontally polarized transverse wave in the workpiece. In this manner, if all four ultrasonic transducers are triggered phase-synchronously, that is Δt=0, α equals zero so that the horizontally polarized transverse waves are irradiated into the workpiece perpendicular to the surface of the workpiece. If the individual ultrasonic transducers are operated with a phase-delay of Δt, during which an ultrasonic wave, for example, reaches from an ultrasonic transducer S1 to the transducer S2, that covers the distance D, the main lobe of the horizontally polarized transverse waves developing inside the workpiece forms an angle α of 90° with the normal of the surface of the workpiece. Depending on the choice of Δt, the main lobe can be varied as desired between 0° and 90° inside the workpiece.

The preceding description, which relates to a transmission operation, can be transferred inversely also to the reception of shear horizontal waves from a workpiece.

Figure 5:
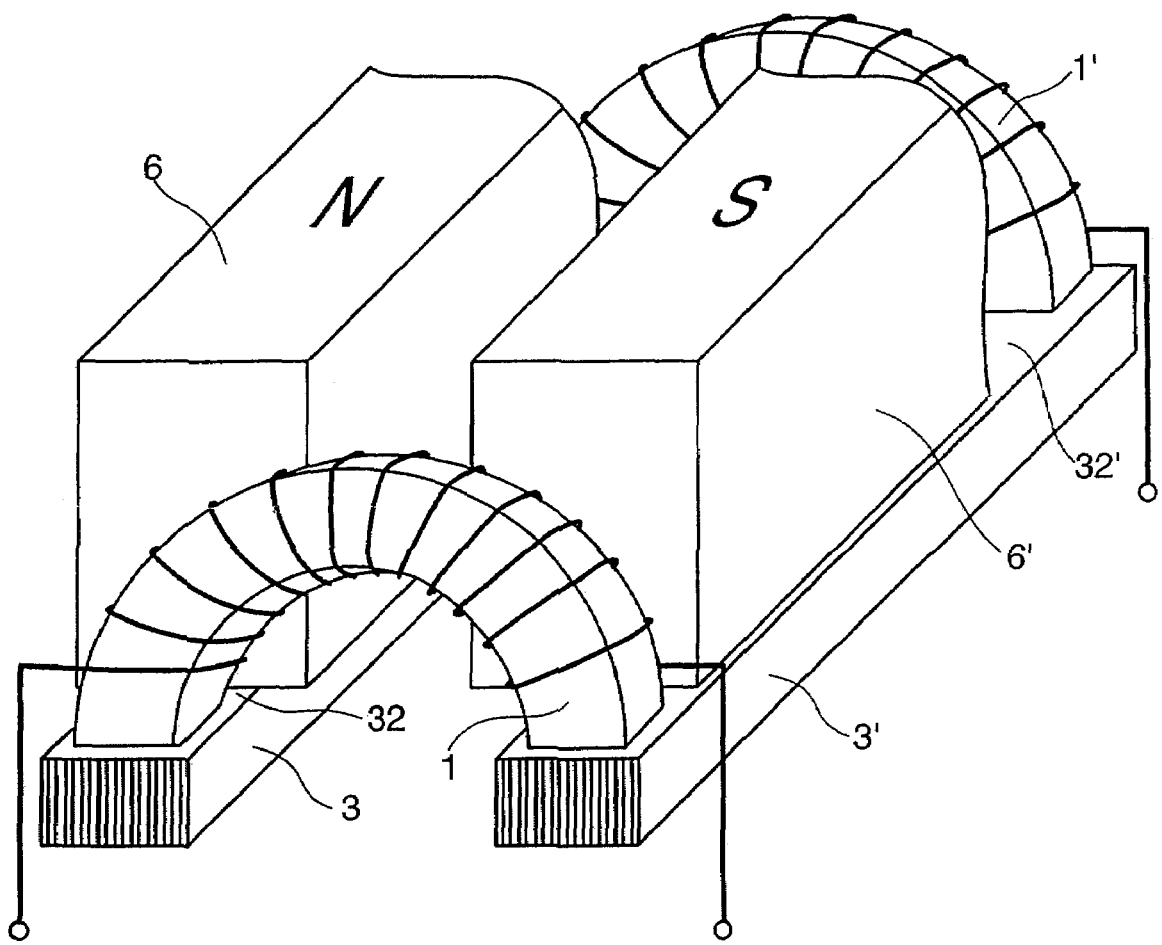
FIG. 5 shows an electromagnetic ultrasonic transducer having two flux guide pieces which are spanned in bridge-like manner by two semi-toroidal magnetic cores.

Another embodiment of an electromagnetic ultrasonic transducer designed according to the present invention is shown in FIG. 5. The transducer is provided with two magnetic flux guide pieces 3 and 3' disposed in parallel at a distance from each other. The upper sides 32 and 32' of the two magnetic flux guide pieces 3 and 3' are connected to the front ends of the two semi-circular-shaped toroidal cores 1 and 1'. The two magnetic flux guide pieces 3 and 3' are thus connected to each other in a bridge-like manner by the toroidal cores 1 and 1'. Moreover, the preferred embodiment shown in FIG. 5 has two counter pole permanent magnets 6 and 6' resting on the respective magnetic flux guide pieces 3 and 3'. Triggering the coil arrangements of the individual toroidal cores 1 and 1' occurs in such a manner that dynamic magnetic fields directed in opposite directions are generated in the magnetic flux guide pieces 3 and 3', causing eddy currents in the workpiece, which are oriented perpendicular to the longitudinal extension of the magnetic flux guide pieces 3 and 3' as well as in opposite directions. Due to the opposite poled permanent magnets 6 and 6', shear forces directed in the same direction develop at skin depth inside the workpieces under the flux guide pieces, thereby creating linearly polarized transverse waves with ultrasonic waves propagating perpendicularly to the surface of the workpiece. Therefore, the arrangement shown in FIG. 5 can be considered to be a normal probe for generating and detecting linearly polarized transverse waves having a large aperture, comparable to the arrangement which has only a single electromagnetic line transducer according to the type of setup of the preferred embodiment shown in FIG. 1.

Figure 6:
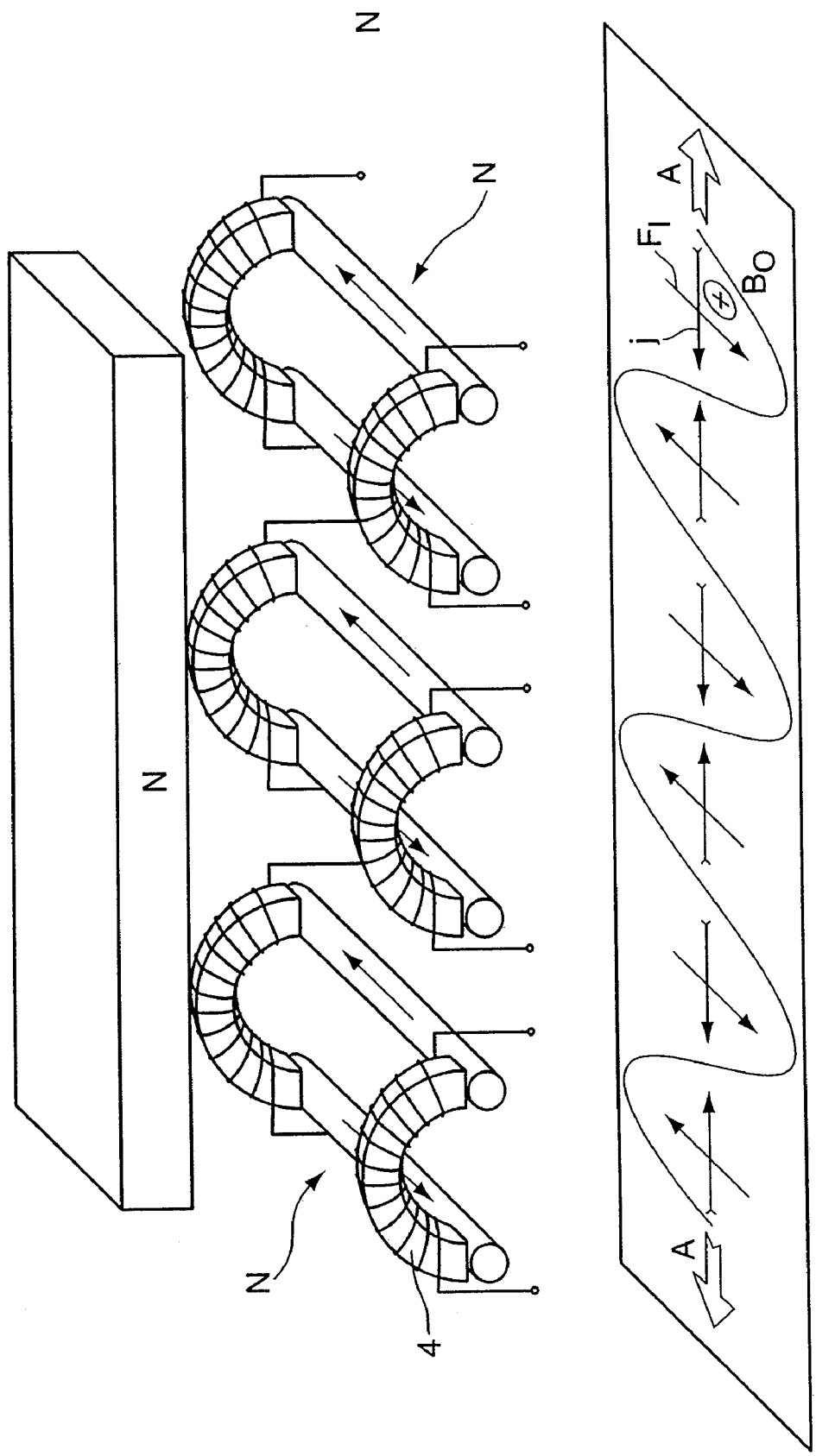
FIG. 6 shows a multiplicity of electromagnetic ultrasonic transducers according to FIG. 5.

FIG. 6 shows an arrangement of three normal probes disposed side by side according to the basic setup of the ultrasonic transducer depicted in FIG. 5. The three normal probes N disposed side by side are switched with their respective high-frequency coils 4 so that in the adjacent flux guide pieces, the direction of the dynamic magnetic fields are oriented in opposite directions, that is there is a phase difference of 180° between the directly adjacent high-frequency magnetic fields. Due to the oriented magnetic flux of the dynamic magnetic fields being directed in opposite directions, the eddy currents which are oriented perpendicular to the direction of the dynamic magnetic fields are coupled into the surface of the workpiece. If a uniform static magnetic field is superimposed, the eddy currents j generate Lorentz forces $F_l$ directly under the respective flux guide pieces 3. The Lorentz forces $F_l$ under the adjacent flux guide pieces are directed in opposite directions and therefore produce shear forces inside the workpiece thereby generating shear horizontal transverse waves. The coil wavelength, which corresponds to the half oscillation wavelength of the SH wave, is determined by the distance between the directly adjacent flux guide pieces. The irradiation direction of the shear horizontal waves is oriented perpendicular to the individual flux guide pieces 3, indicated by the arrows A directed in opposite directions according to FIG. 6.

The embodiment shown in FIG. 6 comprises, in particular, a selective use of a large-area unipolar magnet 6 which is decisively able to suppress the disturbing Barkhausen noise in the region of the individual transducer elements.

Figure 7:
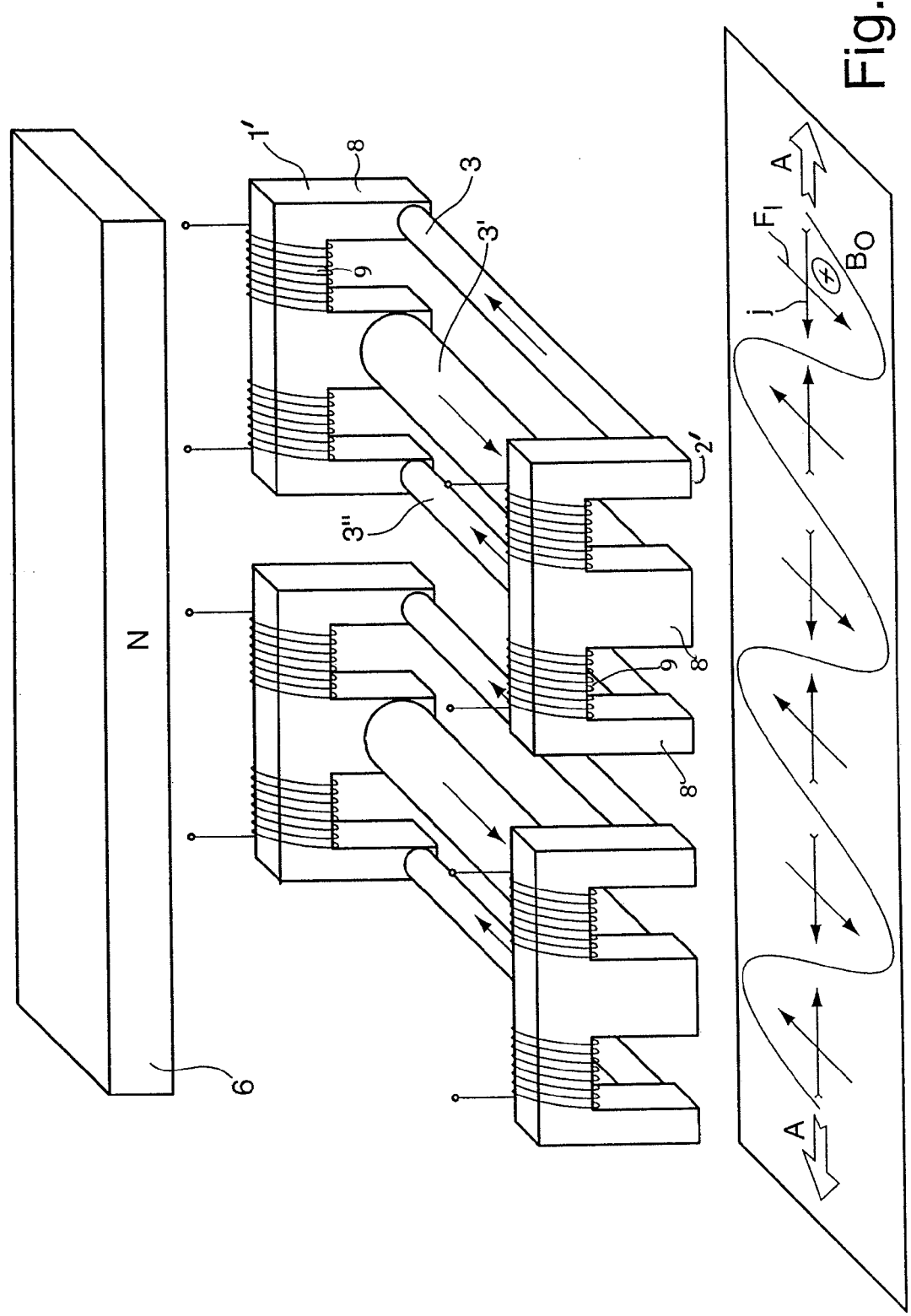
FIG. 7 shows a cross section of M-shaped magnetic cores, which each span in a bridge-like manner three magnetic flux guide pieces.

FIG. 7 shows an embodiment very similar to the embodiment of FIG. 6 for generating shear horizontal waves. In contrast to FIG. 6, in FIG. 7, the core segments 1' are in the form of m-shaped coil cores, with two m-shaped coil cores each being provided with three flux guide pieces 3, 3' and 3". The M shaped cores 1' include parallel pieces 8 with face front ends 2' and are joined by connection parts 9. The coils provided around the coil cores 1 are switched so that high-frequency magnetic fields directed in opposite directions develop in the longitudinal direction of the flux guide pieces located adjacent to each other in parallel. Superimposition of the high-frequency magnetic fields by a static magnetic field generated by the permanent magnet 6, and oriented perpendicular to the surface of the workpiece over the high-frequency magnetic fields causes eddy currents directed in opposite directions inside the workpiece under the directly adjacent flux guide pieces. These eddy currents produce Lorentz forces which are also directed in opposite directions and are responsible for the shear forces required to generate horizontally polarized transverse waves.

LIST OF REFERENCES 1 toroidal core
2 front end
3 flux guide piece
31 and 32 surfaces of the flux guide piece
4 coil arrangement
41 transmission coil
42 reception coil
5 electrical contacts
6 permanent magnet
7 workpiece
8 eddy current

The invention claimed is:

1. An electromagnetic ultrasonic transducer for coupling media free generation and/or reception of ultrasonic waves as linearly polarized transverse waves into and from a workpiece, having at least one unit for converting the ultrasonic waves inside the workpiece and including a coil for generating, and/or detecting a high-frequency magnetic field, a premagnetizing unit for generating a quasi-static magnetic field which superimposes the high-frequency magnetic field in the workpiece, with the coil being torus shaped on at least one partially toroidal magnetic core or at least one magnetic core including parallel pieces, and each core including two front ends which can be turned to face the workpiece; and wherein the front ends of each magnetic core, which can be turned to face the workpiece, are connected directly or indirectly to a magnetic flux piece which has a surface which faces the workpiece and which connects the front ends to each other.

2. The electromagnetic ultrasonic transducer according to claim 1, wherein for generating ultrasonic waves the coil is connected to a high-frequency generator for generating the high-frequency magnetic fields.

3. The electromagnetic ultrasonic transducer according to claim 1, wherein for detecting ultrasonic waves the coil is connected to an amplifier unit and/or to an evaluation unit.

4. The electromagnetic ultrasonic transducer according to claim 1, comprising a transmission coil for generating the high-frequency magnetic field which is connected to a high-frequency generator and a reception coil for detecting the high-frequency magnetic field which is connected to an amplifier unit and/or to an evaluation unit.

5. The electromagnetic ultrasonic transducer according to claim 1, wherein the magnetic flux guide piece comprises a rod and contain soft magnetic material.

6. The electromagnetic ultrasonic transducer according to claim 1, wherein the magnetic flux guide piece comprises a stack of soft magnetic elements or an electrically nonconductive material containing soft magnetic particles distributed in the form of a matrix.

7. The electromagnetic ultrasonic transducer according to claim 1, wherein the front ends of the at least one magnetic core are fused with the magnetic flux guide piece.

8. The electromagnetic ultrasonic transducer according to claim 1, wherein the permagnetizing unit is located directly or indirectly on an upper side of the magnetic flux guide piece facing away from the workpiece.

9. The electromagnetic ultrasonic transducer according to claim 1, wherein the premagnetizing unit is a permanent magnet or an electromagnet.

10. The electromagnetic ultrasonic transducer according to claim 1, wherein the premagnetizing unit permits the quasi-static magnetic field to be introduced into the workpiece perpendicular to the surface of the workpiece.

11. The electromagnetic ultrasonic transducer according to claim 1, wherein the premagnetizing unit is an electromagnet which introduces a quasi-static magnetic field horizontally into the surface of the workpiece.

12. An electromagnetic ultrasonic transducer for coupling media free generation and/or reception of ultrasonic waves as linearly polarized transverse waves into and from a workpiece, having at least one unit for converting the ultrasonic waves inside the workpiece and including coils for generating, or detecting a high-frequency magnetic field, a premagnetizing unit for generating a quasi-static magnetic field which superimposes the high-frequency magnetic field in the workpiece, with the coils being torus shaped on at least two partially toroidal magnetic cores or at least two magnetic cores including parallel pieces, including two front ends which can be turned to face the workpiece;
- at least two magnetic flux guide pieces;
- one front end of a magnetic core is connected directly or indirectly to one of the at least two magnetic flux guide pieces and another front end of a magnetic core is connected directly or indirectly to the another of the at least two magnetic flux guide pieces; and
- one front end of another magnetic core is connected directly or indirectly to one of the at least two magnetic flux guide pieces and the another front end of the another magnetic core is connected directly or indirectly to the another of the at least two magnetic flux guide pieces which are separated from the first magnetic core; and wherein
- the magnetic flux guide pieces each have a surface facing the workpiece.

13. The electromagnetic ultrasonic transducer according to claim 12, wherein the at least two magnetic cores each have two parallel pieces connected via a connection piece, the front ends being located at the ends of the two parallel pieces;
- between each parallel piece at least one further parallel piece is located which is connected on one side to the connection piece at an end of which another front end is located; and
- at least one further magnetic flux guide piece connects front ends of the parallel pieces of both magnetic cores to each other.

14. The electromagnetic ultrasonic transducer according to claim 12, wherein for generating ultrasonic waves the coils are connected to a high-frequency generator for generating the high-frequency magnetic fields.

15. The electromagnetic ultrasonic transducer according to claim 12, wherein for detecting ultrasonic waves the coils are connected to an amplifier unit and/or to an evaluation unit.

16. The electromagnetic ultrasonic transducer according to claim 12, comprising a transmission coil for generating a high-frequency magnetic field which is connected to a high-frequency magnetic generator and a reception coil for detecting the high-frequency magnetic field which is connected to an amplifier unit and/or to an evaluation unit.

17. The electromagnetic ultrasonic transducer according to claim 12, wherein the magnetic flux guide pieces each comprise a rod and contain soft magnetic material.

18. The electromagnetic ultrasonic transducer according to claim 12, wherein the magnetic flux guide pieces comprise a stack of soft magnetic board elements or an electrically nonconductive material containing soft magnetic particles distributed in the form of a matrix.

19. The electromagnetic ultrasonic transducer according to claim 12, wherein the front ends of the magnetic cores are fused with the magnetic flux guide pieces.

20. The electromagnetic ultrasonic transducer according to claim 12, wherein the permagnetizing unit is located directly or indirectly on an upper side of one of the magnetic flux guide pieces facing away from the workpiece.

21. The electromagnetic ultrasonic transducer according to claim 12, wherein the premagnetizing unit is a permanent magnet or an electromagnet.

22. The electromagnetic ultrasonic transducer according to claim 12, wherein the premagnetizing unit permits the quasi-static magnetic field to be introduced into the workpiece perpendicular to the surface of the workpiece.

23. The electromagnetic ultrasonic transducer according to claim 12, wherein the premagnetizing unit is an electromagnet which introduces a quasi-static magnetic field horizontally into the surface of the workpiece.

24. An arrangement for coupling media free generating and/or for receiving ultrasonic waves as linearly polarized transverse waves into and from a workpiece; wherein
- at least two electromagnetic ultrasonic transducers according to claim 2 are spaced apart so that in longitudinal directions of the respective magnetic flux guide pieces individual ultrasonic transducers are aligned in parallel.

25. The arrangement according to claim 23, wherein the premagnetizing unit of individual ultrasonic transducers are the same, or a single premagnetizing unit extends over all magnetic flux guide pieces of the ultrasonic transducers.

26. A use of the arrangement according to claim 23 for generating and/or detecting horizontally polarized transverse waves, wherein the coils of the at least two electromagnetic ultrasonic transducers are operated by phase-array triggering.

27. A use of the arrangement according to claim 26, wherein the coils of the electromagnetic ultrasonic transducers are triggered consecutively with a time-delayed phase trigger signal so that when ultrasonic waves are generated, the ultrasonic waves which enter the workpieces have a direction which is dependent on the phase triggering and have a main direction of propagation movable between 0° and 90° in relation to a normal to the workpiece.

28. A use of the arrangement according to claim 25, wherein for generating ultrasonic waves inside the workpiece, the coils of the individual ultrasonic transducers are triggered so that in two directly adjacent magnetic flux guide pieces, magnetic flux passes therein respectively oriented in opposite directions.

29. An arrangement for coupling media free generating and/or for receiving ultrasonic waves which are linearly polarized into and from a workpiece; wherein
- at least two electromagnetic ultrasonic transducers according to claim 2 are spaced apart from each other so that longitudinal directions of the respective magnetic flux guide pieces of the ultrasonic transducers are aligned in parallel.

30. An arrangement for coupling media free generating and/or for receiving ultrasonic waves which are linearly polarized into and from a workpiece; wherein
- at least two electromagnetic ultrasonic transducers according to claim 13 are spaced apart and from each other so that longitudinal directions of the respective magnetic flux guide pieces of the ultrasonic transducers are aligned in parallel.

* * * * *